United States Patent
Ninov et al.

(10) Patent No.: US 9,682,997 B2
(45) Date of Patent: Jun. 20, 2017

(54) PHARMACEUTICAL FORMULATIONS CONTAINING 3-(4-CINNAMYL-L-PIPERAZINYL) AMINO DERIVATIVES OF 3-FORMYLRIFAMYCIN SV AND 3-FORMYLRIFAMYCIN S AND A PROCESS OF THEIR PREPARATION

(71) Applicants: Adipharm EAD, Sofia (BG); Bozhidar Lyubenov Fudlov, Sofia (BG); Lyibomir Bozhidarov Fudlov, Sofia (BG); Kiril Asenov Ninov, Sofia (BG); Velichka Ilieva Apostolova-Dimova, Sofia (BG); Evtimia Ivanova Stefanova, Sofia (BG); Rossen Krumov Koytchev, Berlin (DE); Ditchev Consulting OOD, Sofia (BG)

(72) Inventors: Kiril Asenov Ninov, Sofia (BG); Velichka Ilieva Apostolova-Dimova, Sofia (BG); Evtimia Ivanova Stefanova, Sofia (BG); Rossen Krumov Koytchev, Berlin (DE); Rumyana Gueorguieva Konstantinova, Sofia (BG)

(73) Assignees: Adipharm EAD, Sofia (BG); Bozhidar Lyubenov Fudlov, Sofia (BG); Lyibomir Bozhidarov Fudlov, Sofia (BG); Kiril Asenov Ninov, Sofia (BG); Velichka Ilieva Apostolova-Dimova, Sofia (BG); Evtimia Ivanova Stefanova, Sofia (BG); Rossen Krumov Koytchev, Neuenhagen (DE); Dichev Consulting OOD, Sofia (BG)

(*) Notice: Subject to any disclaimer, the term of this patent is extended or adjusted under 35 U.S.C. 154(b) by 0 days.

(21) Appl. No.: 14/421,364

(22) PCT Filed: Aug. 9, 2013

(86) PCT No.: PCT/BG2013/000041
§ 371 (c)(1),
(2) Date: Feb. 12, 2015

(87) PCT Pub. No.: WO2014/026254
PCT Pub. Date: Feb. 20, 2014

(65) Prior Publication Data
US 2015/0368263 A1 Dec. 24, 2015

(30) Foreign Application Priority Data

Aug. 13, 2012 (BG) ........................................ 111288

(51) Int. Cl.
C07D 491/00 (2006.01)
A61K 31/395 (2006.01)
A61K 31/495 (2006.01)
C07D 498/08 (2006.01)
A61K 31/496 (2006.01)
A61K 9/48 (2006.01)

(52) U.S. Cl.
CPC .......... *C07D 498/08* (2013.01); *A61K 9/4866* (2013.01); *A61K 31/496* (2013.01)

(58) Field of Classification Search
CPC ... C07D 491/00; A61K 31/395; A61K 31/495
See application file for complete search history.

(56) References Cited

U.S. PATENT DOCUMENTS

| | | |
|---|---|---|
| 4,002,752 A | 1/1977 | Cricchio et al. |
| 4,193,920 A | 3/1980 | Konstantinova et al. |
| 4,918,066 A | 4/1990 | Kump |
| 5,095,108 A | 3/1992 | Konstantinova et al. |
| 6,476,036 B1 | 11/2002 | Konstantinova et al. |

FOREIGN PATENT DOCUMENTS

BG 48618 A1 4/1991

OTHER PUBLICATIONS

International Search Report for International Application No. PCT/BG2013/000041, mailed Dec. 5, 2013.

*Primary Examiner* — Bruck Kifle
(74) *Attorney, Agent, or Firm* — Peter J. Ims; Westman, Champlin & Koehler, P.A.

(57) ABSTRACT

The present invention related to a process of preparation of pharmaceutically acceptable formulations containing as active substance 3-(4-cinnamyl-1-piperazinyl)-amino derivatives of 3-formylrifamycine SV and 3-formylrifamycine S, which possess high activity against Gram-positive and Gram-negative microorganisms, as well as against tuberculous micobacteria (including atypical and rifamycin resistant), and to a method for the preparation of 3-(4-cinnamyl-1-piperazinyl)-amino derivatives of 3-formylrifamycine SV and 3-formylrifamycine S. The method for the preparation of pharmaceutical compositions is readily feasible, and does not require special equipment for its implementation. The process for preparing the compounds is characterized by high yield and purity, using an environmental clean solvent—ethanol and water in the preparation and isolation of substances, and the absence of residual organic solvents in the final product.

19 Claims, No Drawings

PHARMACEUTICAL FORMULATIONS CONTAINING 3-(4-CINNAMYL-L-PIPERAZINYL) AMINO DERIVATIVES OF 3-FORMYLRIFAMYCIN SV AND 3-FORMYLRIFAMYCIN S AND A PROCESS OF THEIR PREPARATION

CROSS REFERENCE TO RELATED APPLICATION

This application is a Section 371 National Stage Application of PCT/BG2013/000041, filed Aug. 9, 2013, and published as WO2014026254 on Feb. 20, 2014, which claims priority and benefits of Bulgarian Patent Application No. 111288, filed Aug. 13, 2012, the entire contents of which are incorporated herein by reference.

FIELD OF THE INVENTION

The present invention related to a process of preparation of pharmaceutically acceptable formulations containing as active substance 3-(4-cinnamyl-1-piperazinyl)-amino derivatives of 3-formylrifamycine SV and 3-formylrifamycine S, which possess high activity against Gram-positive and Gram-negative microorganisms, as well as against tuberculous micobacteria (including atypical and rifamycin resistant), and to a method for the preparation of said active compounds. The pharmaceutical compositions containing active compounds, subject of the invention, may find use as drugs in medical practice, for the prophylaxis and treatment of various diseases caused by Gram-positive and Gram-negative microorganisms and by tuberculous mycobacteria (including atypical and rifamycin resistant).

BACKGROUND OF THE INVENTION

In the literature there are described a variety of pharmaceutical compositions for the treatment and prophylaxis of the above mentioned diseases.

It is known the compound 3-(4-methyl-1-piperazinil)-iminomethyl rifamycin SV-Rifampicin [U.S. Pat. No. 4,193,020], which is characterized by activity against Gram-positive and Gram-negative microorganisms and against *Mycobacterium* tbc.

It is known the compound [U.S. Pat. No. 5,095,108], 3-(4-cinnamyl-1-piperazinyl)-iminomethyl rifamycin SV with Formula Ia:

Formula Ia

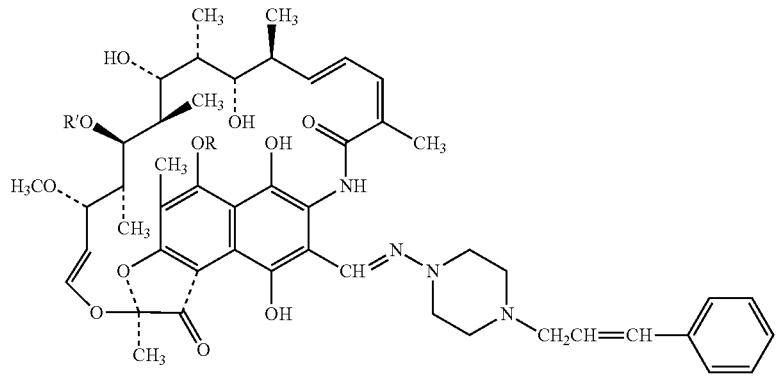

where
R=H and R$^1$=CH3COO which has been shown in in vivo tests, higher therapeutic effect in comparison to rifampicin, and considerably longer serum half-life and a low acute toxicity.

It is known the sodium salt of the above compound [U.S. Pat. No. 6,476,036], with formula Ib Formula Ib

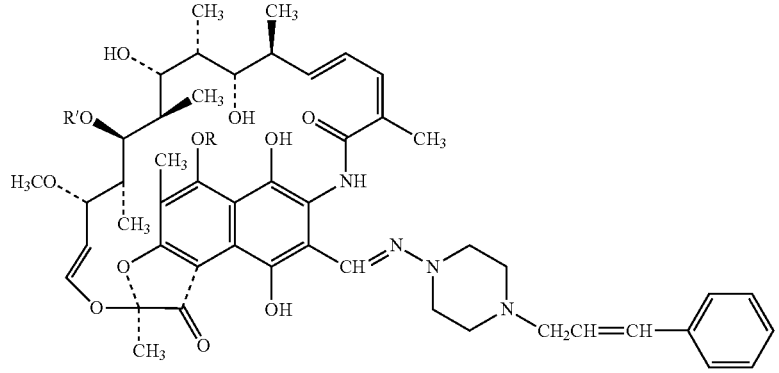

where

R═Na and R¹═CH3COO which is characterized by good solubility in water, faster resorption and better pharmacokinetic properties in in vivo experiments.

Methods are known for the preparation of rifamycin derivatives, including the compound Ia, wherein the 3-formylrifamycin SV, dissolved in tetrahydrofuran, ethyl acetate, chloroform or a mixture of two of these solvents is condensed with an appropriately substituted N-aminopiperazin, then the reaction mixture was concentrated, and the product is recrystallized from an organic solvent, such as acetone or isopropanol [U.S. Pat. No. 4,193,920, U.S. Pat. No. 4,002, 752, BG 48618]. A disadvantage of the known methods is the relatively low yield (from 55% to 80%), and the necessity of purifying the product by recrystallization, and further processing of the mother liquors, which greatly complicates the process. By applying the method they use large amounts of organic solvents, which create additional difficulties in regeneration and environment.

A significant disadvantage is the presence of residual solvents (tetrahydrofuran, chloroform, acetone, isopropanol) in the final product, which, due to specific structure of anzamycin molecule can not be removed even after extensive drying under reduced pressure. Quantities of these solvents, found by gas chromatography, remains above the limits set out in EP 5.0/5.4 Known is a method for preparing a sodium salt (compound Ib) [U.S. Pat. No. 6,476,036], which comprises reacting equimolar amounts of a compound Ia with sodium methanolate, ethanolate or isopropanolate in a medium of the corresponding alcohol. The product was isolated by distilling off the solvent under reduced pressure and recrystallization from isopropanol.

The method is not efficient enough, as to give a relatively low yield of the product, while there is a need for recrystallization, in addition, in the final product is observed presence of residual organic solvents whose quantities are above the limits set out in EP 5.0/5.4

The above mentioned patent application [U.S. Pat. No. 6,476,036] describes another process for the preparation of the sodium salt, which is carried out in aqueous medium, adding to the suspension of 3-formylrifamycin SV water solution of sodium hydroxide and the resulting aqueous solution was subjected to lyophilisation.

The yield in this case was almost quantitative, but due to strong alkaline reaction medium product contains a number of impurities and needs recrystallisation from isopropanol, which leads to a significant reduction in yield and the presence of residual solvents in final product A disadvantage of the known methods is the relatively low yield (from 55% to 80%), and the necessity of purifying the product by recrystallization, and further processing of the mother liquors, which greatly complicates the process. Another disadvantage of the method is the use of organic solvents in large quantities, which creates difficulties in their regeneration, respectively, while protecting the environment. Another major drawback is the presence of residual solvents (tetrahydrofuran, chloroform, acetone, isopropanol) in the final product, which, due to specific structure of anzamycin molecule can not be removed and after extensive drying under reduced pressure. Quantities of these solvents, found by gas chromatography, remains above the limits set out in EP 5.0/5.4

Due to low solubility of rifamycins in ethyl alcohol the use of ethanol leads to a falling of the finished product as a crystalline residue and its direct isolation by filtration, without the necessity of distilling off the solvent in advance.

At the same time the ethanol makes it difficult to carrying out the condensation in a conventional manner. It is generally accepted to a solution of 3-formylrifamycin SV in tetrahydrofuran or chloroform to add a solution of N-substituted aminopiperazin. Using ethyl alcohol as the reaction medium, 3-formylrifamycin SV remains undissolved, and the reaction is carried out in suspension. This leads to incomplete operation of the process and the presence of unreacted 3-formylrifamycin SV in the final product, which requires purification by recrystallization.

There are not known formulations comprising 3-(4-cinnamyl-1-piperazinyl)-amino derivatives of 3-formylrifamycin SV, and 3-formylrifamycin S.

SUMMARY OF THE INVENTION

Taking into account the prior art in this field the task of the present invention is to propose pharmaceutical formulations containing as active compounds 3-(4-cinnamyl-1-piperazinyl)-amino derivatives of 3-formylrifamycin SV and 3-formylrifamycin S, with high biological activity.

Another object of the invention is to provide a process for the preparation of active compounds 3-(4-cinnamyl-1-piperazinyl)-amino derivatives of 3-formylrifamycin SV and 3-formylrifamycin S, which possess high biological activity, providing a very high yield and very high purity, technologically simple in carrying out the process and reduction of its duration.

This object is solved by a pharmaceutical formulations, including the active substance in a mixture of excipients, depending on physico-chemical properties of active ingredient, and function of the excipient.

According to the invention the active substance is a compound, characterized by Formula I and II, as substitutes for R is hydrogen or Na and R1-hydrogen or CH3COO, and its amount in the pharmaceutical composition is from 100 to 600 mg, and the amount of the excipients is from 1.5% to 25% based on the total weight of the mixture.

As active substance are used new rifamycin derivatives with formulas Ic, Id, IIa, IIb, IIc and IId, and compounds of formula Ia and Ib.

According to a preferred embodiment of the invention the amount of active substance is 150 to 300 mg.

According to one embodiment of the present invention as excipients are used microcrystalline cellulose, corn starch, sodium stearyl fumarate, magnesium stearate.

According to a preferred embodiment of the invention active substance from the group of the said active compounds is mixed directly (dry blending) with the excipients and the resulting mixture is filled into capsules, then the capsules are packaged in a suitable way. The present invention is also achieved by a method for the preparation of novel rifamycin derivative, which is carried out by reaction of N1-cinnamyl-N4-aminopiperazin and 3-formylrifamycin SV, wherein to a solution of aminopiperazin was added 3-rifamycin SV, portion wise, in solid form, and after each portion was awaiting its passage into solution. The reaction is performed in the presence of small amounts of acetic acid, at a temperature of 20-30° C. for about 2 hours. Product is obtained as a dark red crystalline precipitate, the reaction mixture is diluted with equal volume of water and after cooling to 5-10° C. was filtered and dried to constant weight.

Compound Ib is prepared by reaction of equimolar quantities of 3-(4-cinnamyl-1-piperazinyl)-iminomethyl rifamycin SV (1a) with sodium methanolate in a medium of ethyl alcohol at room temperature. The resulting solution of the sodium salt of compound Ia is distilled under reduced pressure and a temperature not higher than 60° C., until complete removal of the ethanol, the residue is dissolved in water in the presence of small amounts of sodium ascorbate, and the resulting solution was lyophilized.

The yield of the sodium salt of 3-(4-cinnamyl-1-piperazinyl)-iminomethyl rifamycin SV (compound Ib) is quantitative; the product has a very high purity and does not contain any residual organic solvents.

The new compounds of formulas IIa and IIb are prepared by oxidation of compounds Ia and Ib with manganese dioxide in an alcoholic medium, wherein the hydroquinone structure passes into quinone.

Compounds of formulas Ic, Id, IIe and IId are prepared by reaction of compounds Ia and IIa with a dilute solution of sodium hydroxide or sodium carbonate in aqueous-alcoholic medium, wherein the ester group in 25-position of the molecule, is hydrolyzed, to afford the corresponding 25-desacetil derivatives in the form of sodium salts (compounds Id and IId).

Upon acidification of the ethanol solution of the latter two compounds with dilute hydrochloric acid are received compounds Ic and IIe.

Newly synthesized rifamycin derivatives can be represented by Formula Ic, Id, IIa, IIb, IIc and IId. Those newly compounds have high antibacterial activity, comparable to that of the compounds Ia and Ib. All synthesized compounds were proven by elementary analysis, IR and UV spectra.

where for
IIa-R=H, $R^1$=COCH3
IIb-R=Na, $R^1$=COCH3
IIe-R=H, $R^1$=H
IId-R=Na, $R^1$=H The yield of the sodium salt of 3-(4-cinnamyl-1-piperazinyl)-iminomethyl rifamycin SV (compound Ib) is quantitative; the product has a very high purity and does not contain any residual organic solvents. The method according to the invention is characterized by the fact that, that operations are carried out in sequence and process parameters which give a product of high purity, as there is no need for further purification, and free from residual amounts of organic solvents. The yield was almost quantitative (98% of theory), and the product has a very high purity and does not need further purification, which simplifies the process and reduces its duration. Besides high yield and purity, advantage of the method is the use of environmentally safe solvents in the preparation and isolation of the substance-ethanol and water, and the absence of residual organic solvents in the final product. The method is easy to implement from a technological standpoint and economically advantageous.

The resulting product is suitable for use in the prophylaxis and treatment of diseases caused by Gram-positive and Gram-negative microorganisms as well as for prophylaxis and treatment of diseases caused by *Mycobacterium* tuberculosis (including atypical and rifamycin resistant strains), as according to the invention is suitable the product to be made in a suitable pharmaceutically acceptable formulation.

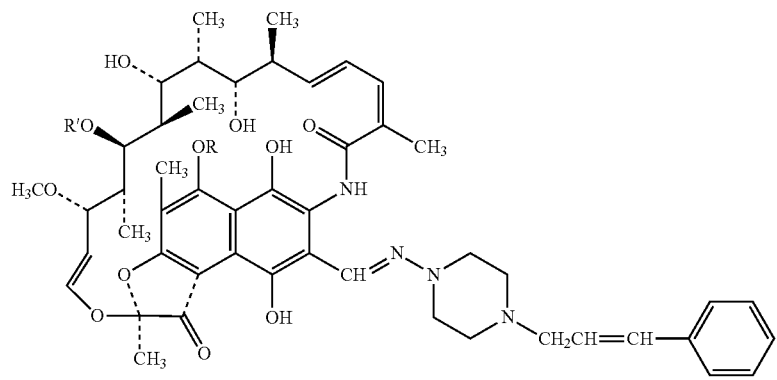

Where for
Ic-R=H, $R^1$=H
Id-R=Na, $R^1$=H

Formula II

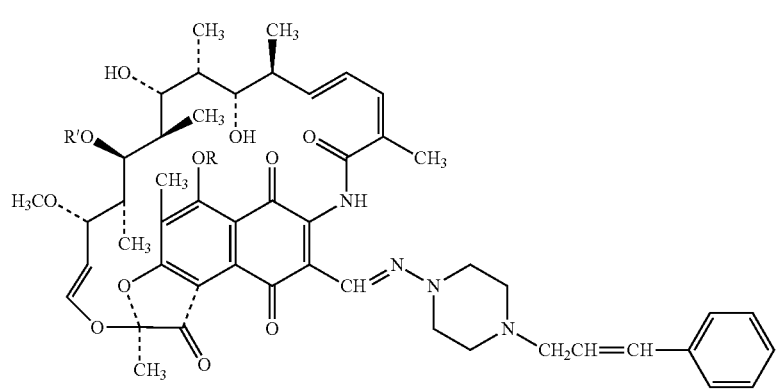

In most cases, this may include, but are not limited to, hard gelatin capsules at a dose depending on the activity of the compound from 100 to 600 mg as a single dose, e.g. 150, 300 or 600 mg and corresponding adjuvants, such as microcrystalline cellulose, starch, magnesium stearate, sodium stearyl fumarate and the like.

Suitably the resulting mixture was filled in capsules, which can be packaged in a suitable manner, for example in aluminum blisters.

PREFERRED EMBODIMENT OF THE INVENTION

Further, the description will be presented examples of the embodiment of the pharmaceutical formulations, and examples of obtaining the active compounds of formulas I and II, and pharmaceutical formulations are not limited to the examples described and may also be applied such embodiments, within the parameters outlined above and ratios.

Example 1

Microcrystalline cellulose (5.60 g) and sodium stearyl fumarate (1.40 g) are sieved and dry-mixed with a pre-weighed amount (30.0 g) of the active ingredient-sodium salt of 3-(4-cinnamyl-1-piperazinyl)-iminomethyl rifamycin SV (compound Ib). After a homogenization, mixture comprising 15.1% of microcrystalline cellulose, 3.8% sodium stearyl fumarate and 81.1% of active substance, is filled into a capsule and then be packaged in a suitable manner, e.g. in aluminum/aluminum blisters. Obtained are 180±5 capsules with an average weight of the contents ~185±9 mg.

Example 2

Prior sieved starch (6.00 g) and sodium stearyl fumarate (1.00 g) are dry-mixed with a pre-weighed amount (30.0 g) of sodium salt of 3-(4-cinnamyl-1-piperazinyl)-iminomethyl rifamycin S (Compound IIb). After a homogenization mixture is obtained with content-16.2% starch, sodium stearyl fumarate 2.7% and 81.1% of the above-described active agent. The mixture is filled into a capsule and then be packaged in a suitable manner in aluminum/aluminum blisters. Obtained are 180±5 capsules with an average weight of the contents ~185±9 mg.

Example 3

Microcrystalline cellulose (3.0 g) and sodium stearyl fumarate (1.0 g) are sieved and dry mixed well with a pre-weighed amount (60.0 g) of sodium salt of 3-(4-cinnamyl-1-piperazinyl)-iminomethyl-25-desacetoxy rifamycin SV (Compound Id). The resulting homogeneous mixture containing microcrystalline cellulose 4.7%, 1.6% sodium stearyl fumarate and as an active ingredient the sodium salt of 3-(4-cinnamyl-1-piperazinyl)-iminomethyl-25-desacetoxy rifamycin SV-93.8%, is filled into capsules, which are packaged in a suitable way in aluminum/aluminum blisters. Obtained are 180±5 capsules with an average weight of the contents ~320 mg±16 mg.

Example 4

Starch (12.50 g) and magnesium stearate (0.75 g) are sieved and dry-mixed well with a pre-weighed amount (37.0 g) of sodium salt of 3-(4-cinnamyl-1-piperazinyl)-iminomethyl-25-desacetoxy rifamycin S (Compound IId). The resulting homogeneous mixture consisting of 12.5% starch, magnesium stearate 1.5% and 74% of active substance is filled into capsules, which are packaged in an appropriate manner. Obtained are 180±5 capsules with an average weight of the contents ~320 mg±16 mg.

Similarly, compositions were prepared with all other derivatives disclosed already in this patent specification.

Example 5

To a solution of 6.3 g (0.0289 gM) N1-cinnamyl-N4-amino piperazine in 200 ml of ethanol is added 1.2 ml of glacial acetic acid. Under stirring and at 20-30° C. to the ethanol solution are added portion wise 20 g (0.0276 gM) 3-formylrifamycin SV after each batch waiting to dissolve. Addition takes about 30 min and depletion of the starting rifamycin SV is monitored by thin layer chromatography. Stirring is continued for 2 h wherein there is a formation of a dark red crystalline precipitate. The reaction mixture is diluted with 200 ml water, stirred for 15 min and cooled to 5° C. The resulting precipitate of 3-(4-cinnamyl-1-piperazinyl) iminomethyl rifamycin SV is filtered and washed with 20 ml water. After drying under vacuum at 70° C. 25 g of a dark red precipitate are obtained, representing 98% of the theoretical yield. The product has purity greater than 98%.

Example 6

To a suspension of 25 g (24.7 g as 100%) of 3-(4-cinnamyl-1-piperazinyl) iminomethyl rifamycin SV (0.0264 gM) in 200 ml of ethanol with stirring 4.88 ml of 30% solution of sodium methoxide (0.0264 gM) is added, wherein the suspension almost immediately pass into solution. The reaction mixture is filtered and the solvent is distilled under vacuum till complete elimination. To the resulting gummy residue 200 ml of water and 1 g of sodium ascorbate is added. The mixture is stirred until complete dissolving, and subjected to lyophilization. Obtained are 25.2 g (99.2% of theory) of the sodium salt of 3-(4-cinnamyl-1-piperazinyl) iminomethyl rifamycin SV in 98% purity.

Example 7

To a solution of 5 g of 3-(4-cinnamyl-1-piperazinyl) iminomethyl rifamycin SV in 150 ml of ethanol, 3 g of manganese dioxide is added, the reaction mixture was stirred for 4 hours, and by thin layer chromatography is monitored the passage of the hydroquinone into a quinone form. The reaction mixture is heated to 50-60° C., and filtered, and the precipitate of MnO2 is washed thoroughly with warmed ethanol. The resulting solution is distilled under vacuum to near dryness. The precipitate is dried in a vacuum oven at 50° C. Obtained are 4.9 g (98.2% of theory) of 3-(4-cinnamyl-1-piperazinyl) iminomethyl rifamycin S. The product is a dark violet crystalline precipitate.

Example 8

To a solution of 5 g of the sodium salt of 3-(4-cinnamyl-1-piperazinyl) iminomethyl rifamycin SV in 150 ml of ethanol 5 g MnO2 is added and the mixture is stirred for 4 hours to complete switching into the quinone form (TLC). The mixture is heated to 50-60° C., filtered and the precipitate of MnO2 is washed thoroughly with hot ethanol. The solution is distilled to about ⅓ of the original volume. The residue is dried in a vacuum oven at 50° C. Obtained are dark violet crystals of the sodium salt of 3-(4-cinnamyl-1-piperazinyl) iminomethyl rifamycin S. Yield 5 g (97.6 of theory).

Example 9

To a solution of 5 g of sodium hydroxide in 100 ml of a 50% aqueous ethanol 5 g of 3-(4-cinnamyl-1-piperazinyl) iminomethyl rifamycin SV is added. Almost immediately, the mixture passes into the solution, in which after 10 min begins to fall bright red precipitate. The mixture is cooled to 10° C., filtered and the precipitate is dried in a vacuum oven at 50° C. Obtained are 4.5 g (92% of theory) of the sodium salt of 25-desacetyl-3-(4-cinnamyl-1-piperazinyl) iminomethyl rifamycin SV.

Example 10

To a solution of 3.5 g of sodium salt of 25-desacetyl-3-(4-cinnamyl-1-piperazinyl) iminomethyl rifamycin SV in 100 ml of ethanol under heating to 40° C., 2 ml of hydrochloric acid diluted in 10 ml water are added. Orange-red solution is obtained, which crystallized upon cooling. The received bright orange precipitate of 25-desacetyl-3-(4-cinnamyl-1-piperazinyl) iminomethyl rifamycin SV is filtered and dried in a vacuum oven at 50° C. Yield 3.3 g (96.5% of theory).

Example 11

The procedure is as in Example 5 but instead of 3-(4-cinnamyl-1-piperazinyl) iminomethyl rifamycin SV is used 3-(4-cinnamyl-1-piperazinyl) iminomethyl rifamycin S. Obtained is sodium salt of 3-(4-cinnamyl-1-piperazinyl) iminomethyl rifamycin S in 90% yield of theory.

Example 12

The product of Example 7 was subjected to the procedure described in Example 6. Prepared is 25-desacetyl-3-(4-cinnamyl-1-piperazinyl) iminomethyl rifamycin S in 95% yield

The invention claimed is:

1. A pharmaceutical formulation comprising a mixture of an active substance and excipient, wherein the active substance has the structure

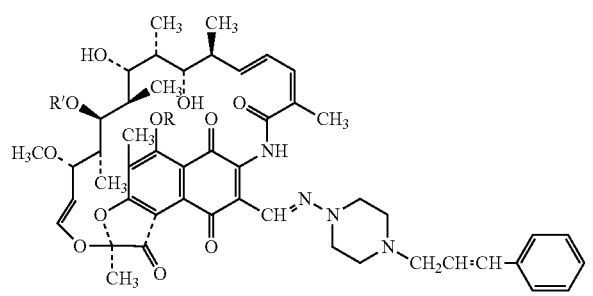

wherein R is H or Na, and R' is COCH3 or H, and wherein the amount of active ingredient per dosage unit is from 100 to 600 mg, and the excipients are present in an amount from 1 to 25% based on the total weight of the mixture.

2. The pharmaceutical formulation according to claim 1 wherein the excipients comprise microcrystalline cellulose and starch.

3. The pharmaceutical formulation according to claim 1 wherein the excipients comprise sliding excipients selected from the group consisting of sodium stearyl fumarate and magnesium stearate.

4. A compound of a formula

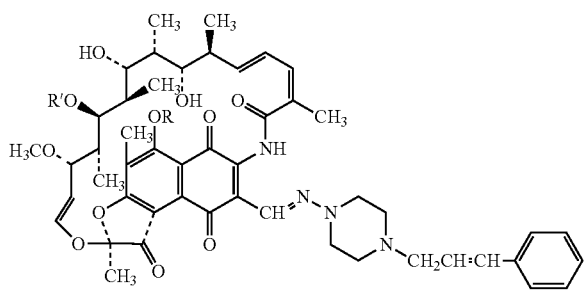

wherein R is H or Na, and R' is COCH3 or H.

5. The compound according to claim 4 wherein R=H and R'=COCH$_3$.

6. The compound according to claim 4 wherein R=Na and R'=COCH$_3$.

7. The compound according to claim 4 wherein R=H and R'=H.

8. The compound according to claim 4 wherein R=Na and R'=H.

9. The pharmaceutical formulation according to claim 1, wherein R=H and R'=COCH$_3$.

10. The pharmaceutical formulation according to claim 1, wherein R=Na and R'=COCH$_3$.

11. The pharmaceutical formulation according to claim 1, wherein R=H and R'=H.

12. The pharmaceutical formulation according to claim 1, wherein R=Na and R'=H.

13. A method of treating a person of diseases and conditions caused by Gram-positive or Gram-negative bacteria, the method comprising:
providing a dosage of an active substance and excipient, wherein the active substance has the structure

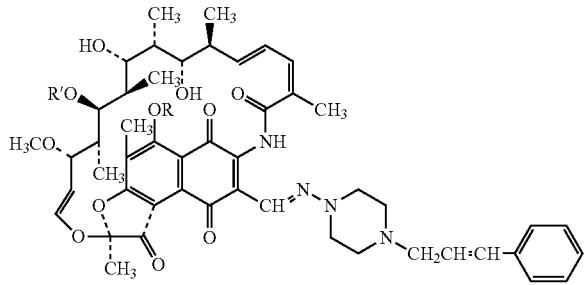

wherein R is H or Na, and R' is COCH3 or H, and wherein the amount of active ingredient per dosage unit is from 100 to 600 mg, and the excipients are present in an amount from 1 to 25% based on the total weight of the mixture.

14. The method of claim 13 and wherein the ailment is caused by tuberculous *mycobacterium*.

15. The method of claim 13 and wherein the ailment is atypical and rifamycin resistant forms of tuberculosis.

16. The method of claim 13 and wherein R=H and R'=COCH$_3$.

17. The method of claim 13 and wherein R=Na and R'=COCH$_3$.

18. The method of claim 13 and wherein R=H and R'=H.

19. The method of claim 13 and wherein R=Na and R'=H.

* * * * *